United States Patent [19]
Fitzpatrick et al.

[11] Patent Number: 5,865,166
[45] Date of Patent: Feb. 2, 1999

[54] ORTHOPEDIC CUSHION

[75] Inventors: Brian Fitzpatrick, Randolph; Ronald Lancaster, South Easton; Robert W. Pekar, Florence, all of Mass.

[73] Assignee: Johnson & Johnson Professional, Inc., Raynham, Mass.

[21] Appl. No.: 17,351

[22] Filed: Feb. 2, 1998

[51] Int. Cl.⁶ .................................................. A61F 5/00
[52] U.S. Cl. ............................ 128/117.1; 128/113.1; 602/13; 602/26
[58] Field of Search ...................... 602/5, 13, 16, 602/26; 128/112.1, 113.1, 117.1, 118.1; 607/108, 114; 5/621–624, 636, 644, 645, 646, 648

[56] References Cited

U.S. PATENT DOCUMENTS

| | | | |
|---|---|---|---|
| 3,745,998 | 7/1973 | Rose | 602/13 X |
| 4,657,003 | 4/1987 | Wirtz | 602/13 X |
| 4,862,879 | 9/1989 | Coombs | 602/13 X |
| 5,316,547 | 5/1994 | Gildersleeve | 602/26 |
| 5,415,625 | 5/1995 | Cassford et al. | 602/26 |
| 5,520,622 | 5/1996 | Bastyr et al. | 602/16 |
| 5,527,268 | 6/1996 | Gildersleeve et al. | 602/26 |
| 5,542,911 | 8/1996 | Cassford et al. | 602/26 |

*Primary Examiner*—Linda C. M. Dvorak

[57] ABSTRACT

A cushion or pad for orthopedic applications is disclosed. The cushion or pad comprises a bladder filled with a combination of spherical objects in a lubricant and an inflatable air bladder. The inflation of the air bladder is used to properly position an orthesis on a patient.

6 Claims, 4 Drawing Sheets

ORTHOPEDIC CUSHION

FIELD OF THE INVENTION

The present invention relates to a cushion or protective padding material that can be employed in orthopedic braces, walkers and other orthesis. The padding material provides improved cushioning between the rigid components of the orthesis and the patient wearing the device.

BACKGROUND OF THE INVENTION

Orthopedic orthesis including knee braces, ankle braces, shoulder braces, hip braces and similar devices are commonly used to stabilize the limbs of the patient after injury. These devices usually comprise a rigid support to immobilize the particular portion of the patients limbs that have been injured and cushioning or padding material between the support and the body of the patient.

The types of supporting materials that have previously been used include a fiber cushion material, foam pads, air bladders and gels of various types, including recently a material comprising a bladder filled with spherical particles in a lubricant which is marketed under the tradename FLOAM, and is available from Tech Form in Salt Lake City, Utah.

Although the above mentioned padding materials has been found to be useful they suffer from the fact that they do not provide adequate support for the bony protuberances in the patients limbs and these bony protuberances have a tendency to bottom or extend through the cushioning material and contact the rigid support structure of the orthesis which causes discomfort to the patient.

SUMMARY OF THE PRESENT INVENTION

The present invention provides an improved cushion material that can readily be used in orthesis of any type such as walkers, knee braces, ankle braces, shoulder braces and hip braces. It finds particular utility as a condyle pad in a knee brace. The cushioning material of the present invention comprises an inflatable air bladder affixed to a bladder which is FLOAM, that is a composite mixture of spherical objects in a lubricant. These two bladders are secured together in a fashion that allows the maximum utilization of the cushioning characteristics of each bladder in the device as will be hereinafter explained.

The two bladders in the device, that is the air bladder and the FLOAM bladder are secured together in a fashion so that the peripheral edges of each bladder is not in contact with the peripheral edge of the other bladder so that the configuration of the cushioning material or cushion pad resembles a bellows. This provides significantly greater support for the limb of the patient which is in contact with the pad. Generally, the air bladder portion of the cushioning pad is in contact with the rigid support of the orthesis and the FLOAM bladder is in contact with the body of the patient.

DETAILED DESCRIPTION OF THE PRESENT INVENTION

Figure 1:
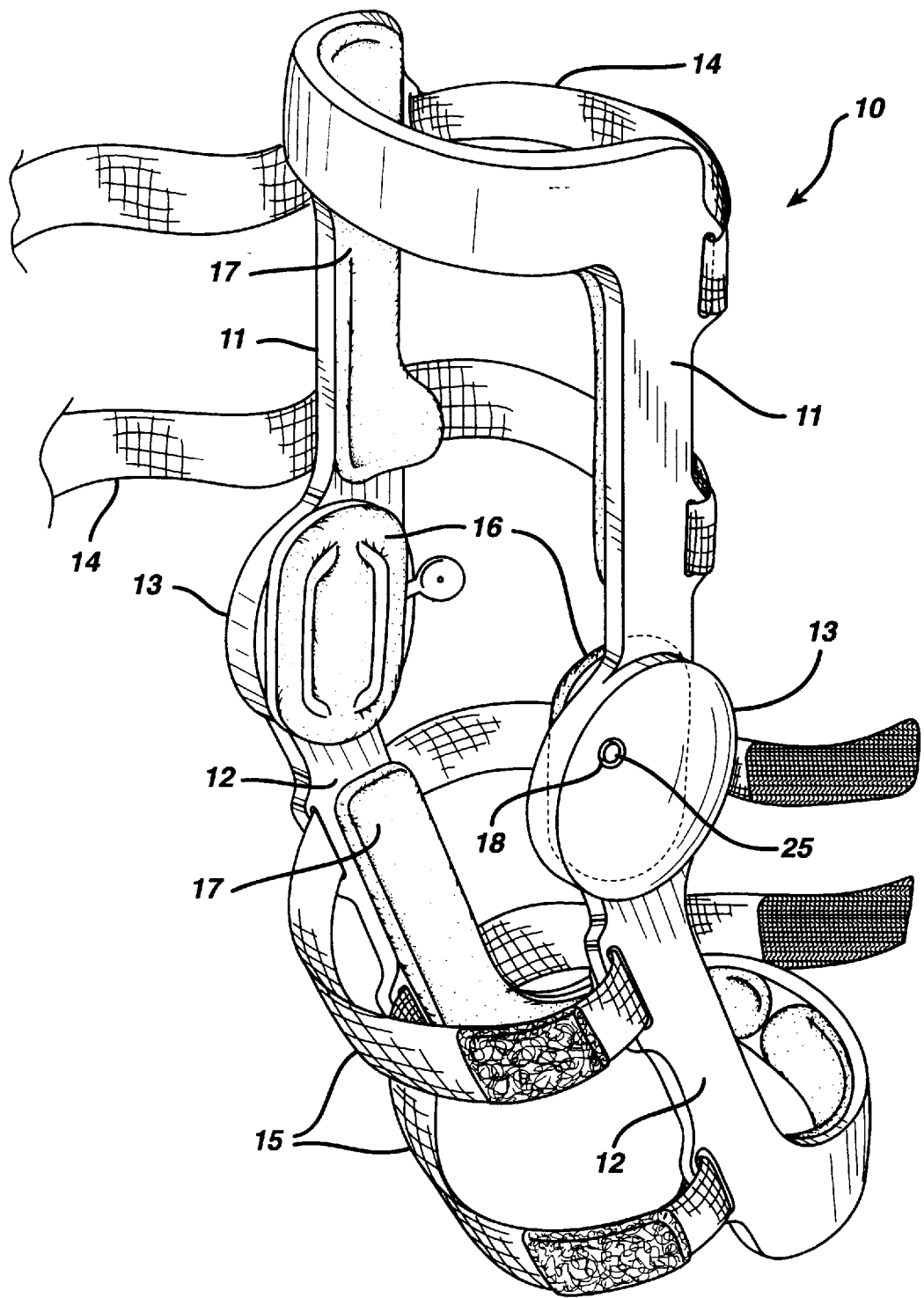
FIG. 1 shows a typical knee brace employing the pad of the present invention as the condylar pad.

Referring to FIG. 1, there is shown an orthopedic knee brace 10 which comprises two upper supports 11 and two lower supports 12. The supports 11 and 12 are joined through hinges 13. The supports are secured to the patient with straps 14 on the upper or thigh portion of the support 11 and straps 15 on the lower or calf portion of the support 12. There are condyle pads 16 which overlie the hinges where the hinges would contact the knee of the patient. There are also pads 17 around the areas where there are straps 18 on the supports 11 and 12 which are also portions of the brace which contact the body of the patient.

Figure 2:
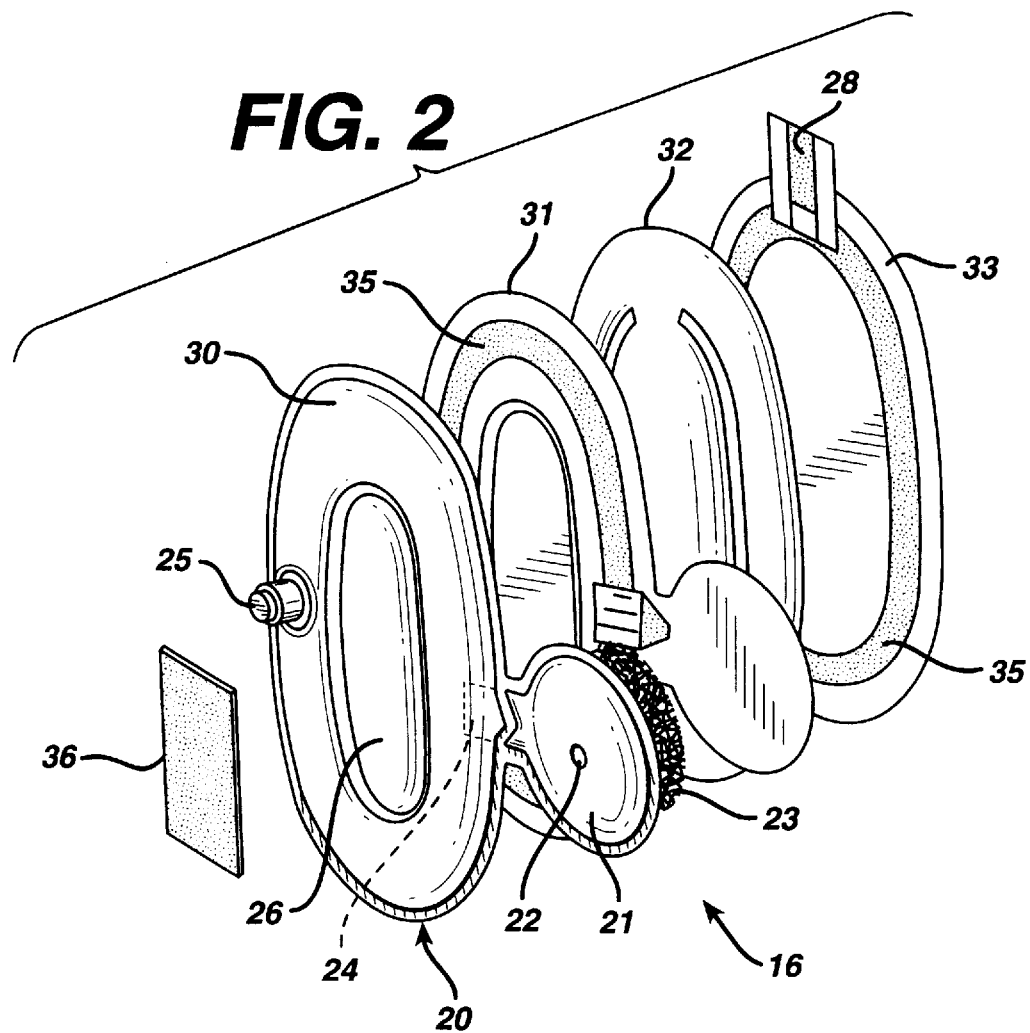
FIG. 2 is an exploded view of the pad of the present invention.

In FIG. 2 there is shown a detailed exploded drawing of the pad of the present invention in a configuration that can be used as condylar pad.

The device of the present invention generally comprises two bladders. The first bladder 20 is an air bladder constructed by securing together two sheets of material 30 and 31. The sheets of material are preferably thermoplastic and are joined together by heat bonding. The air bladder can be inflated with a pump 21 which is integrally connected to the bladder. The pump comprises two layers of a flexible sheet material 27, with a foam layer 23, between the sheets of flexible material. The sheet material is preferably a thermoplastic material that can be heat sealed around its periphery to join the sheets together. There is an opening 22 in the pump which allows air to enter the pump. The pump includes a foam layer 23 which consists of an open cell reticulated flexible elastomeric material such as polyurethane in the interior of the pump which provides resistance to the pumping pressure. There is a check valve 24 between the pump and the bladder itself. The bladder has a release valve 25 which can be depressed to release air from the bladder to adjust the pressure of the air within the bladder. The advantage of the construction of the present invention is the ability to adjust the frame of the brace to apply pressure to either or both sides of the knee to insure proper conformability of the brace to the patient. The bladder shown in the drawing consists of an outer ring which is a race track shape with an inner area which is not inflatable. The air filled bladder is described in greater detail in U.S. Pat. No. 5,144,708, the disclosure which is incorporated herein by reference.

Figure 3:
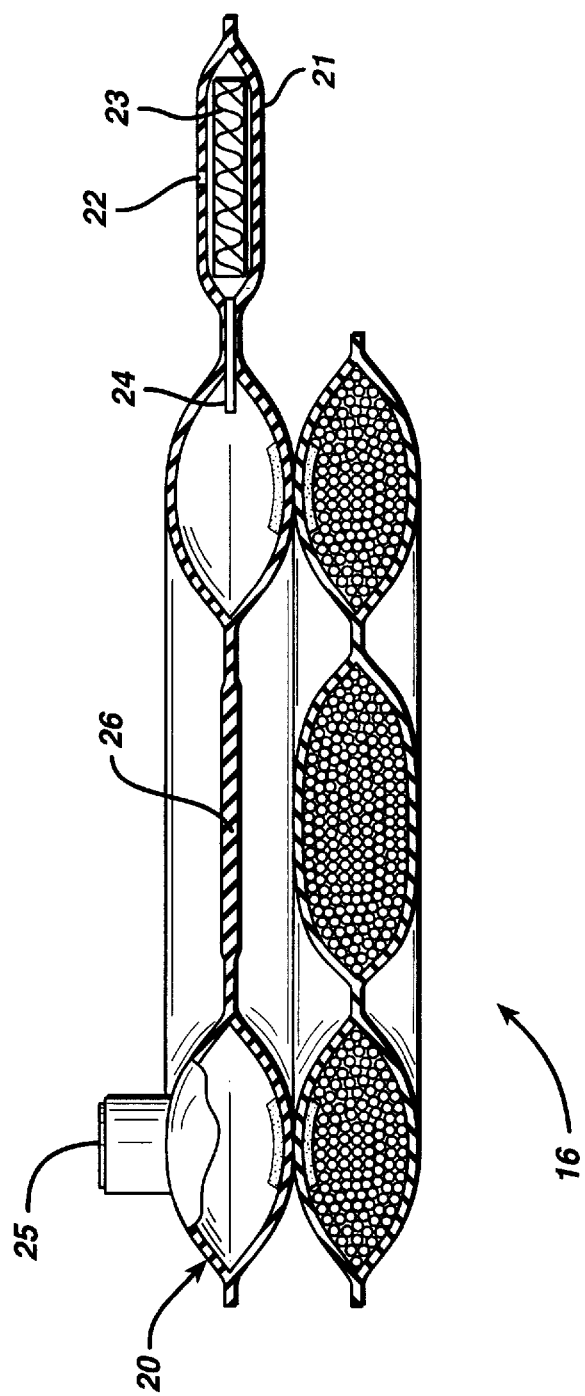
FIG. 3 is a cross sectional view of the pad of the present invention.

The FLOAM bladder consists of two layers of thermoplastic sheet material 31 and 32 which contain particles 33 in a lubricant. This is the bladder that contacts the body. The interior section of the bladder is filled with spherical objects or particles contained in a lubricant. This construction is disclosed in detail in U.S. Pat. No. 5,421,874, which is incorporated herein by reference. The spherical particles in the lubricant can be inserted into the FLOAM pad through a filler tube 28. After filling, the filler tube is sealed at the edge of the bladder and removed. The air bladder and the FLOAM bladder are secured together along a seal line which is at a position spaced inwardly, one inch to one half inch from the peripheral edges of the bladders. The bladders may be secured together by an adhesive or by heat softening or welding the thermoplastic material of each bladder to the adjacent bladder. The positioning of the attachment line of the two bladders is such that the peripheral edges of the bladders are free to expand into a bellow shape as shown in FIG. 3. This provides a greater flexibility in the contact of the FLOAM bladder with the body of the patient and allows a more even pressure distribution to the contours of the limb.

On the interior surface of each of the bladders opposite the seal area there is a release surface 35 which may be a silicone coating or a thin layer of Polytetraflouroethylene. The purpose of the release surface is to prevent the inner surfaces of the bladders from being adhered to each other during the heat sealing process. If the surfaces of the bladders are inadvertently secured together near the periphery, the outer ring of the bladder will be distorted and the bladder will not properly fit the patient. The use of such coatings to prevent bonding of heat sealable films is disclosed in U.S. Pat. No. 5,022,109, the disclosure of which is incorporated herein by reference.

The cushion may be attached to the rigid portion of a brace by any means but is preferably attached by employing a hook and loop device commonly known as a Velcro hook and loop fastener by securing one portion 36 in FIG. 2, either the hook or the loop portion, to the air bladder and securing the other portion to the rigid support where the cushion pad is to be affixed.

Figure 4:
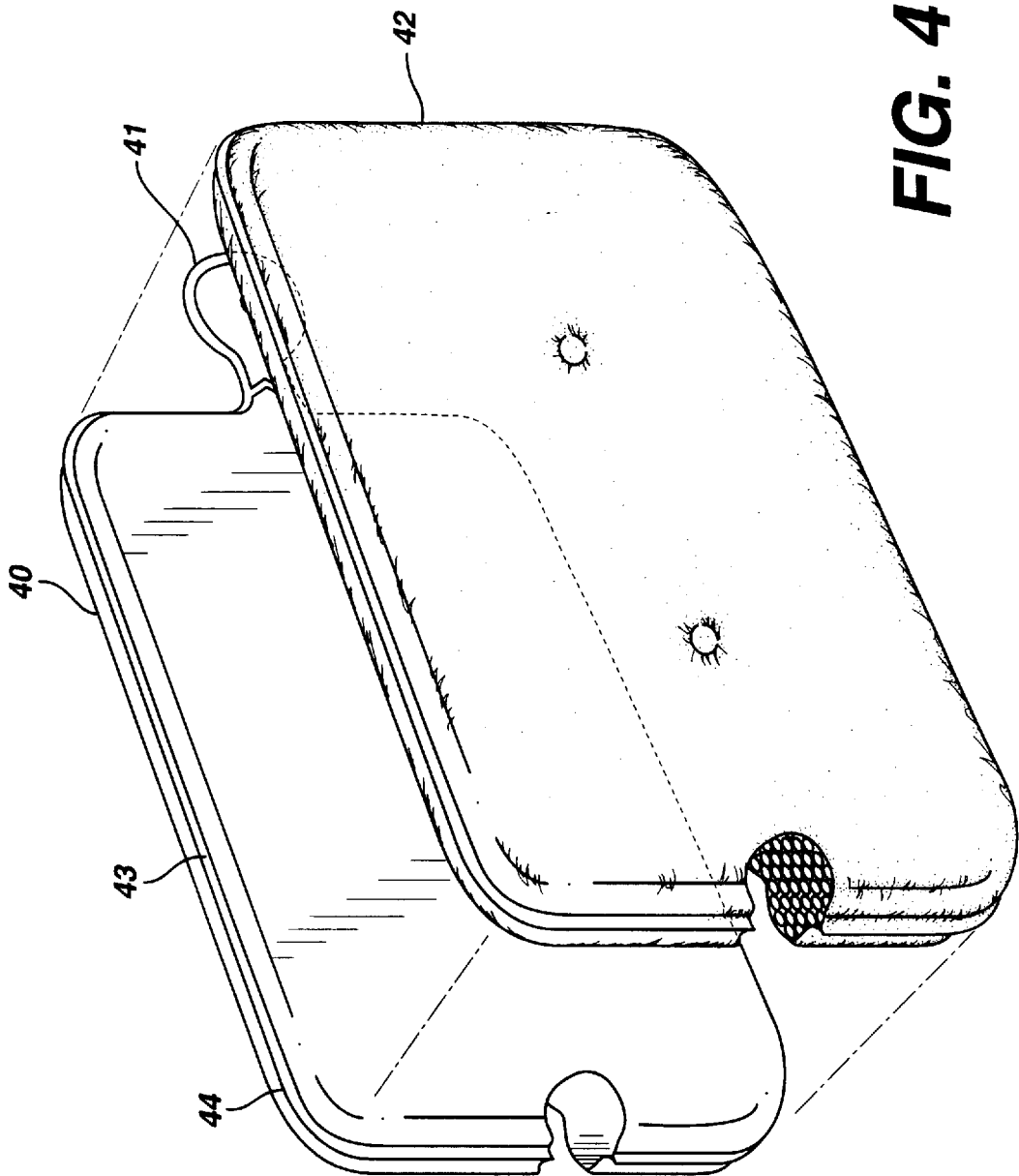
FIG. 4 shows a cross sectional view of the pad of the present invention configured for use in a hip brace.

The cushion construction shown in FIGS. 1, 2 and 3 is designed for a knee brace. The cushion shown in FIG. 4 is of a configuration that is suitable for a hip brace. The cushion comprises a large air bladder 40, to which is connected an air pump 41, which is of the same general construction as discussed above and shown in FIG. 3. The FLOAM bladder 42, contains particles in a lubricant. The bladders are sealed to each other along a line 43, which is spaced inwardly from the periphery 44, of the bladder. The interior of each of the bladders includes a release area (not shown) which is located in the interior of the bladder opposite the line on which the bladders are sealed together. The air bladder release valve 25 is accessible through an opening 18 in the cover of the condylar pad.

A series of tests were performed to determine the pressure that could be exerted by the present pad on a patient's knee to support the knee in position in the brace. All testing was conducted on the MTS Sintech Upgrade machine instrumented with a 1000 lbs. load cell. All tests would be conducted between two flat surfaces, a platen was fitted onto the free end of the load cell and a metal stand with a flat upper surface was placed on the testing platform.

First, the load cell was calibrated by the autocalibration feature of Testworks and with a load of 4.0 lbs. Then, each condylar pad was placed on the metal stand in the testing frame with the FLOAM side facing upwards in the direction of the load cell. In addition, as a depressurization valve protrudes from the air side of the pads, a flat metal plate with a tapped hole was placed beneath each pad such that the valve would fit into the hole and the upper surface of the pad would be in the same plane as the compressive surfaces.

Each pad was then compressed to a thickness of 0.264 in. for approximately 30 sec. to flatten the surface of the FLOAM component and, by momentarily opening the depressurization valve, to ensure that only a minimal level of air remained in the air side. The actuator was then raised away from the pad until the surface of the platen was not touching the pad and the load cell was re-zeroed. The actuator was then moved downward until a pre-load of –0.5 lbs. ((–) meaning compressive load) was registered by the load cell to ensure that most of the pad surface was touching the platen before testing. After the load cell was re-zeroed, the condylar pad was then inflated by hand until no further increase in load was measured by the load cell and the maximum load was read from the computer screen on the Testworks load output. This procedure was repeated for a total of 10 condylar pads.

The Air/FLOAM condylar pads were able to produce an average pressure of 15.913 ±1.670 lbs. Obviously, the separation distance between plates must be observed, as it would have a substantial effect on generated pressure.

Results of Preliminary Compression Testing of Condylar Pads

| Pad No. | Load (lbs) | |
| --- | --- | --- |
| 1 | 14.06 | |
| 2 | 14.49 | |
| 3 | 16.21 | |
| 4 | 16.00 | |
| 5 | 18.34 | |
| 6 | 14.6 | |
| 7 | 13.97 | |
| 8 | 17.14 | |
| 9 | 18.49 | |
| 10 | 15.83 | |
| | Mean | 15.913 |
| | Standard Deviation | 1.669904 |
| | Co. Variance | 0.10494 |

What is claimed is:

1.) A protective pad comprising an air filled first bladder having an air impervious sealed outer periphery, a second bladder having a sealed outer periphery, said second bladder containing a composite mixture of spherical objects and a lubricant, said first bladder being attached to said second bladder along an attachment line spaced inwardly toward the center of the pad from the outer periphery of the first and second bladder, to maintain a transverse space between the outer periphery of the first bladder and the outer periphery of the second bladder when the first bladder is inflated with air.

2.) The protective pad of claim 1 in which the spherical objects have a diameter of between 10 and 200 microns.

3.) The protective pad of claim 1 in which the first bladder comprises two superimposed sheets of a thermoplastic material of substantially the same dimensions sealed together at their outer periphery.

4.) The protective pad of claim 1 in which the second bladder comprises two superimposed sheets of thermoplastic material of substantially the same dimensions sealed together at their outer periphery.

5.) The protective pad of claim 1 in which the sheets of thermoplastic material of each bladder are sealed together along a second seal line spaced inwardly toward the center of the pad from the circumferential line of attachment of the bladders to each other.

6.) The protective pad of claim 1 further comprising an air pump and an air release valve connected to said first bladder to allow the air pressure in said first bladder to be adjusted.

* * * * *